United States Patent
France et al.

(10) Patent No.: US 6,495,172 B1
(45) Date of Patent: Dec. 17, 2002

(54) METHOD OF USING STEAM IRONING OF FABRICS AS A WAY OF CAUSING REDUCTION OF PHYSIOLOGICAL AND/OR SUBJECTIVE REACTIVITY TO STRESS IN HUMANS

(75) Inventors: Paul Amaat France, West Chester, OH (US); Arseni V. Radomyselski, Hamilton, OH (US)

(73) Assignee: Procter & Gamble, Cincinnati, OH (US)

( * ) Notice: Subject to any disclaimer, the term of this patent is extended or adjusted under 35 U.S.C. 154(b) by 0 days.

(21) Appl. No.: 09/868,342

(22) PCT Filed: Dec. 8, 1999

(86) PCT No.: PCT/IB99/01966

§ 371 (c)(1),
(2), (4) Date: Jun. 15, 2001

(87) PCT Pub. No.: WO00/37092

PCT Pub. Date: Jun. 29, 2000

Related U.S. Application Data

(60) Provisional application No. 60/113,347, filed on Dec. 21, 1998.

(51) Int. Cl.$^7$ ............................................. A61K 35/78
(52) U.S. Cl. .................. 424/725; 424/733; 424/742; 424/747; 424/746; 424/765; 424/736
(58) Field of Search ................................ 424/733, 742, 424/725, 747, 746, 765, 736

(56) References Cited

U.S. PATENT DOCUMENTS

| | | | |
|---|---|---|---|
| 4,152,272 A | | 5/1979 | Young |
| 4,670,463 A | | 6/1987 | Warren et al. |
| 5,064,543 A | | 11/1991 | Coffindaffer |
| 5,318,503 A | * | 6/1994 | Lord |
| 5,409,619 A | | 4/1995 | DeRenzo |
| 5,432,154 A | | 7/1995 | deHeij |
| 5,526,595 A | | 6/1996 | Daulasim et al. |
| 5,645,751 A | | 7/1997 | Haley |
| 5,725,833 A | * | 3/1998 | Crafton |
| 5,830,109 A | * | 11/1998 | Juarez |
| 5,980,880 A | * | 11/1999 | Love |

FOREIGN PATENT DOCUMENTS

| | | |
|---|---|---|
| DE | 29 600 628 U1 | 1/1996 |
| GB | 2304740 A | 3/1997 |
| GB | 2313133 A | 11/1997 |

OTHER PUBLICATIONS

A. Delongis et al., Health Psychology, 1981, 1(2), pp. 119–136.
R.B. Devereux, Circulation 68, 1983, No. 3, pp. 470–476.
T.G. Pickering et al., Clinical and Experimental Hypertension, 1982, A4(4&5), pp. 675–693.
H. Benson et al., Science, 1971, 173, pp. 740–742.
Surwit et al., Behavioral Approaches to Cardiovascular Disease, Behavorial medicine Series, Academic Press, 1982, pp. 129–156.
G. Buchbauer et al., Aromatherapy—Use of Fragrances and Essential Oils and Medicaments, Flavour and Fragrance journal, 1994, vol. 9, pp. 217–222.
The Psychophysiological Effects of Odors, Aromachology—Review of the latest researches on the effects of odors, Takasago Intern'l. Corp., Japan; Koryo, No. 168 (1990).
C.A. Dunn, Fragrances That Make a House a Home, happi, Sep. 1998, pp. 75–84.

* cited by examiner

Primary Examiner—Francisco Prats
Assistant Examiner—Susan D. Coe
(74) Attorney, Agent, or Firm—C. Brant Cook; K. W. Zerby; Steve W. Miller

(57) ABSTRACT

A method of using steam ironing of fabrics as a way of causing reduction of physiological and/or subjective reactivity to stress in a human is provided. The method includes the steps of providing a stress reducing composition comprising one or more of a volatile natural essential oil and water. The composition is adapted to not cause staining of fabrics. The method includes delivering the stress reducing composition into a liquid container of a steam iron and heating the steam iron. The method further includes releasing vapors of the stress reducing composition produced within the liquid container of the steam iron upon heating into ambient air. The method still further includes the step of causing reduction of physiological and/or subjective reactivity to stress in the human by one of more of transdermal ingestion or inhalation of the vapors by the human.

8 Claims, No Drawings

METHOD OF USING STEAM IRONING OF FABRICS AS A WAY OF CAUSING REDUCTION OF PHYSIOLOGICAL AND/OR SUBJECTIVE REACTIVITY TO STRESS IN HUMANS

This application is a 371 of PCT/B99/01966, filed Dec. 8, 1999, which claims benefit to U.S. Provisional application Ser. No. 60/113,347, filed Dec. 21, 1998.

TECHNICAL FIELD

The present invention relates to a method of using steam ironing of fabrics as a way of causing reduction of physiological and/or subjective reactivity to stress in humans that have been subjected to such stress. More particularly, the invention relates to a method for using steam ironing of fabrics as a way of causing reduction of physiological and/or subjective reactivity to stress in humans by employing the beneficial effects of aromatherapy during steam ironing.

BACKGROUND OF THE INVENTION

Human reactivity to stress is insidious because even though it does not directly incapacitate a human, researchers have discovered that stress decreases productivity, and eventually may lead to illness. This reactivity to stress can be brought about by the repetitive or chronic strains of everyday life. Research in this area has shown that the daily hassle, as measured by self-report, is more strongly associated with somatic health than are life event scores. That is, the frequency and intensity of hassles are significantly related to somatic illness (A. Delongis, et al, Health Psychology, 1981, 1 (2), 119–136). Chronic reactivity, as measured by elevated blood pressure, particularly systolic blood pressure, is correlated with disease. By use of a portable blood pressure-measuring device, it has been shown that regularly recurring stress (specifically that occurring in the work place) correlates with the occurrence of left ventricular hypertrophy. In particular, it has been shown that the correlation exists in patients showing elevated systolic blood pressures while actually engaged in their workday tasks (R. B. Devereux, et al, Circulation 68, No. 3, 470–476, 1983). In another study, blood pressures measured every 15 minutes for 24 hours in 25 normal subjects, 25 borderline subjects and 25 established hypertensive subjects showed significantly higher blood pressures at work than at home, at the physician's office or while sleeping. (T. G. Pickering, et al, Clinical and Experimental Hypertension, A4(4&5), 675–693 1982).

The classical techniques used for controlling reactivity to stress include biofeedback, meditation and drugs. With respect to biofeedback, in one study, researchers used a constant-cuff technique and gave feedback and reinforcement for the lowering of systolic blood pressure in seven patients, five of whom had been diagnosed as having essential hypertension. The five patients with hypertension responded positively, all showing significant decreases in their systolic blood pressures after 30 sessions of training (Benson, H., Shapiro, D., Tursky, B., and Schwartz, G. E., Science, 1971, 173, 740–742). Other physiological parameters used for biofeedback training include pulse transit time, electromyogram activity and skin resistance biofeedback.

The type of relaxation training techniques used for the treatment of hypertension are variations of either certain Eastern meditative disciplines, progressive relaxation techniques or autogenic training. These techniques are intended to lower blood pressure by promoting physical and mental relaxation. Specific examples of such techniques are disclosed in U.S. Pat. No. 4,670,463 issued on Jun. 2, 1987 to Craig B. Warren et al. A review of the use of biofeedback and relaxation techniques for the treatment of hypertension can be found in: Surwit, et al, "Behavioral Approaches to Cardiovascular Disease", Behavorial Medicine Series, Academic Press, 1982, 139–156.

Chemical agents have also been used to modify the effects of stress, tension, anxiety and dysphoria throughout recorded history, such as ethanol, bromide salts and barbiturates. Again, U.S. Pat. No. 4,670,463 issued on Jun. 2, 1987 to Craig B. Warren et al. offers a good account of such other methods.

Aromatherapy is another method for reducing physiological and/or subjective reactivity to stress in humans. In fact, it is currently a burgeoning industry that has led to the commercial success of a vast variety of aromatherapy oils, soaps, perfumes, massage treatments and the like. The term "Aromatherapy" is intended herein to mean the use of plant-derived substances; volatile substances derived from plants for the treatment of health problems. Generally, the volatile fraction—the essential oil fraction—of the plant-derived substance is used. The use of the volatile fractions of plants for treatment of various ailments is reviewed in the following three monographs: (1) J. Valnet, "The Practice of Aromatherapy", Destiny Books (Division of Inner Traditions International, Ltd.), New York, N.Y., 1982; (2) R. Tisserand, "The Art of Aromatherapy", Destiny Books (Division of Inner Traditions International, Ltd.), New York, N.Y., 1983; and (3) A. Leung, "Encyclopedia of Common Natural Ingredients", J. Wiley & Sons Publishing Co., New York, N.Y., 1980. A detailed analysis of the aromatherapy folk medicine literature suggested that a number of essential oils commonly used in perfumery might have a multiplicity of medical effects. Some of these oils are employed in the practice of this invention. U.S. Pat. No. 4,670,463 issued on Jun. 2, 1987 to Craig B. Warren et al. offers a good account of such aromatherapy oils.

While different aromatherapy techniques have been used in the past, such as bath gels, bath oils, soaps, aromatherapy perfumes, there has been the need for having some other novel method that exploits the well documented benefits of aromatherapy in stress reduction in a manner that is easy to use and practice on a daily basis.

The inventors of the subject invention have discovered that by using plant-derived substances common to the fields of perfumery and aromatherapy in a steam iron along with water, can result in an easy to practice method for reducing stress. The dose levels of the aromatherapy oils and perfumes, however, differ from those normally employed in either perfumery or aromatherapy and the mode of application differs from those normally employed for aromatherapy. But by using selected doses of such oils and perfumes in the steam iron, an individual can experience some degree of stress relaxation while at the same time accomplishing the essential task of ironing fabrics.

Thus although the materials employed in the practice of this invention are known in the art and are known to exhibit physiologic activity, insofar as the inventors of the subject invention have been able to ascertain, no suggestion relevant to reducing physiological and/or subjective reactivity to stress during the process of steam ironing of fabrics is made in the prior art.

It has been desirable to have an easy to use method for causing the reduction of physiological and/or subjective reactivity to stress in a human being subjected to stress conditions (such as the daily hassles of the work place). It has been further desirable to develop a method for causing reduction of physiological and/or subjective reactivity to stress in a human being subjected to conditions of stress by administering to such a human an effective amount of an aromatherapeutic active material. It has still further been desirable to have a method for causing the reduction of physiological and/or subjective reactivity to stress in a human being subjected to stress conditions by administering transdermally and/or by means of inhalation an effective amount of an active material in an aesthetically pleasing form, such as, for example, a perfume or an aromatherapeutic oil.

The present invention overcomes the problems, as set forth above.

BACKGROUND ART

U.S. Pat. No. 4,670,463 issued on Jun. 2, 1987 to Craig B. Warren et al. discloses various types of aromatherapy oils and perfumes, and is incorporated herein by reference.

U.S. Pat. No. 5,526,595, issued on Jun. 18, 1996 to Denis Daulasim et al. relates to a steam iron equipped with a cartridge for treating water or cloth to be ironed. This patent, which discloses enabling embodiments of steam irons and vaporization chamber mechanisms, is incorporated by reference.

SUMMARY OF THE INVENTION

The invention meets the needs above by providing a method of using steam ironing of fabrics as a way of causing reduction of physiological and/or subjective reactivity to stress in a human, a method for promoting aromatherapeutic effect in a human while the human is engaged in a task of steam ironing a fabric, and a method of using aromatheraphy during steam ironing for causing reduction of physiological and/or subjective reactivity to stress in a human.

In one aspect of the present invention, the method of using steam ironing of fabrics as a way of causing reduction of physiological and/or subjective reactivity to stress in a human includes the steps of providing a stress reducing composition comprising one or more of a volatile natural essential oil, and water. The composition is adapted to not cause staining of fabrics. The method includes delivering the stress reducing composition into a liquid container of a steam iron and heating the steam iron. The method further includes releasing vapors of the stress reducing composition produced within the liquid container of the steam iron upon heating, into ambient air. The method still further includes the step of causing reduction of physiological and/or subjective reactivity to stress in the human by one or more of transdermal ingestion or inhalation of the vapors by the human.

In another aspect of the present invention, the method for promoting aromatherapeutic effect in a human while the human is engaged in a task of steam ironing a fabric includes the steps of providing an aromatherapeutically active composition comprising one or more of a volatile natural essential oil, and water. The oil is adapted for promoting an aromatherapeutic effect in a human. The composition is also adapted to not cause staining of fabrics. The method also includes delivering the aromatherapeutically active composition into a liquid container of an steam iron and heating the steam iron. The method also includes releasing vapors of the aromatherapeutically active composition produced within the liquid container of the steam iron upon heating, into ambient air. The method further includes promoting aromatherapeutic effect in the human by one or more of transdermal ingestion or inhalation of the vapors by the human.

In yet another aspect of the present invention, the method of using aromatherapy during steam ironing for causing reduction of physiological and/or subjective reactivity to stress in a human includes the steps of providing an aromatherapeutically active composition comprising one or more of a volatile natural essential oil, and water. The composition is adapted to not cause staining of fabrics. The method includes delivering the aromatherapeutically active composition into a liquid container of a steam iron and heating the steam iron. The method includes releasing vapors of the aromatherapeutically active composition produced within the liquid container of the steam iron upon heating, into ambient air. The method also includes causing reduction of physiological and/or subjective reactivity to stress in the human by one or more of transdermal ingestion or inhalation of the vapors by the human.

DETAILED DESCRIPTION OF THE INVENTION

In the preferred embodiment of the present invention, the method of using steam ironing of fabrics as a way of causing reduction of physiological and/or subjective reactivity to stress in a human includes the steps of providing a stress reducing composition comprising one or more of a volatile natural essential oil, and water. Desirably, the stress reducing composition comprises one or more of a volatile natural essential oil present in an amount in a range of from about 0.05% to about 5% by weight of said composition, and preferably from about 0.5% to about 2.0%.

Volatile Natural Essential Oil

In one embodiment, the volatile natural essential oil is selected from the group consisting of hops extract, elder flower extract, eucalyptus oil, spearmint oil, clary sage oil, and mixtures thereof. In another embodiment, the volatile natural essential oil is selected from the group consisting of rosewood oil, juniper oil, and mixtures thereof. In yet another embodiment, the volatile natural essential oil is selected from the group consisting of witch hazel, mentha piperita oil, orange oil, sweet violet leaf oil, hops extract, elder flower extract, and mixtures thereof.

In the preferred embodiment, the volatile natural essential oil is selected from the group consisting of nutmeg oil, mace extract, neroli oil, valerian oil, myristicin, isoelemicin, elemicin, and mixtures thereof.

A number of essential oils commonly used in perfumery can also have a multiplicity of medical and aromtherapeutic effects. Some of these oils are employed in the practice of this invention.

Neroli oil is the essential oil obtained from orange blossoms. Neroli oil has a folk medicine history as being an anti-depressant, aphrodisiac, antiseptic, antispasmodic and of having digestive and sedative activity. The anecdotal literature suggests that neroli oil is an effective sedative and anti-depressant and that it may be used for insomnia, hysteria, states of anxiety and depression. Neroli is an effective sedative-antidepressant oils: it may be used for insomnia, hysteria, states of anxiety and depression. It is known to calm and slow down the mind. It also has a notable action on the heart, diminishing the amplitude of heart muscle contraction, hence its use in palpitations or other types of cardiac spasm. Derived from this is its use in panicky, hysterial, fearful types of people—those who upset themselves unnecessarily, and become over wrought over nothing. Neroli is a valuable remedy for shock, or for disorders caused by sudden shock, or fear, causing a strain on the heart. It is valuable in chronic diarrhoea, when this is related to long-standing stress or fear. Oil of neroli also has a pronounced action on the skin. Like lavender and geranium it can be used with benefit on any type of skin. It is totally non-irritant and may be used where there is irritation or redness. It is said to be useful for dry skin and broken veins. It is one of the oils which acts on a cellular level stimulating the elimination of old cells and the growth of new ones. Neroli makes a luxurious, relaxing, and deodorant bath oil.

Orange-flower water is soothing, digestive, carminative. It makes a very useful, mild remedy for infants' colic, and its sedative action helps to send them to sleep.

Valerian oil is the essential oil obtained from the root of Valeriana officinalis. The folk medicine literature lists the valerian root (fresh or dried) as being useful as an antispasmodic, carminative, stomachic and sedative. It has been used to treat migraine, insomnia, hysteria, fatigue and stomach cramps that cause vomiting. Valeriana is known to have a general calming and sedative effect on the central nervous system, to induce sleep and rest, spasms of the stomach, intestines and blood vessels, nervous heart conditions. Further acknowledgment as appetizer, headache relief, hysteria, epilepsy, tape worm, diarrhoea, lose stomach, fever. The chemical constituents, pharmacology and known uses of valerian are reviewed in: "Herbal Remedies Used in Sedative and Antirheumatic Preparations: Part I", Phillipson, et al, The Pharmaceutical Journal, Jul. 21, 1984, pages 80–82.

Another potentially interesting plant substance is nutmeg which was important in medicine as well as well as in cooking. It was used as a therapeutic by Arab physicians as early as the 7th Century A.D. for treatment for disorders of the digestive system, kidney disease, pain and lymphatic ailments. Nutmeg is a significant item in the Hindu Pharmacopeia wherein it has been prescribed for fever, consumption, asthma and heart disease. Nutmeg is employed by folk practitioners in India as an analgesic and sedative. The fraction of nutmeg responsible for the mild hallucinogenic activity is suggested by the literature to be the aromatic fraction of the oil containing safrole, methyleugenol, eugenol, methylisoeugenol, myristicin, elemicin, isoelemicin and methoxyeugenol as the major components. The myristicin-elemicin fraction of oil of nutmeg produces many of the activities of crude ground nutmeg but lacks adequate potency to explain the nutmeg intoxication syndrome on a quantitative basis. Nutmeg and synthetically-made myristicin show a mild degree of monoamine oxidase inhibiting activity. The monoamine oxidase activity is found in the volatile component of nutmeg. Nutmeg oil, known as myristica fragrans, or myristicaceae, is the essential oil from the kernel of the fruit of the nutmeg tree. The stone of the fruit is enclosed within a husk which, when dried, is known as mace. "Mace Extract" is an aromatic essence extracted from mace. "Nutmeg Butter" is a fixed oil obtained by hot-pressing the nutmeg kernels, and contains myristine, butyrin, olein, palmitine and stearine. The essence contains 80% pinene and camphene, 8% dipentene, 6% terpenic alcohols, (linalool, borneol, terpineol and geraniol), 4% myristicin and various substances such as eugenol and safrol. Valnet, "The Practice of Aromatherapy", (supra) states that, for external use:

(a) "nutmeg butter" is used in liniments for the treatment of rheumatic pains and toothaches; and
(b) "nutmeg butter" is used in the form of "nerve balm" for treatment of rheumatic pains, the form being a mixture of the essences of rosemary and clove together with nutmeg butter. A form of nutmeg oil, Myristica castaneifolia (Myristacaceae) Fiji is described as possessing biological activity, specifically in the antitumor field, in U.S. Pat. No. 4,352,797 issued on Oct. 5, 1982, the specification for which is incorporated by reference herein.

The essential oils described above are also common perfumery ingredients as described in Arctander, "Perfume and Flavors Materials of Natural Origin", published by the author in 1960. (Mace extract at columns 391–393; neroli oil at columns 435–437; nutmeg oil at columns 442–445; and valerian oil at columns 637–638).

Low Foaming Surfactant

The stress reducing composition can also include a low foaming surfactant in a range of from about 0.1% to about 5% by weight. The preferred surfactants are low foaming non-ionic surfactants including nonionic alkoxylated surfactants, especially ethoxylates derived from primary alcohols, and blends thereof with more sophisticated surfactants, such as the polyoxypropylene/polyoxyethylene/polyoxypropylene reverse block polymers. The PO/EO/PO polymer-type surfactants are well-known to have foam suppressing or defoaming action. Various other forms of low foaming surfactants may be used in this application, and such forms are well known to one skilled in the art and thus, need not be listed here.

In the preferred embodiment, the stress reducing composition includes a foam suppressant in a range of from about 0.1% to about 5% by weight. Examples of foam suppressants include alkyl phosphonic acid esters and alkyl acid phosphate esters. Other foam suppressants include, for example, the known silicones. It must be noted that various other types of foam suppressants, well known to one skilled in the art may be utilized, so long as such foam suppressants do not cause fabric staining.

Optionally, the stress reducing composition may include an anti-dye transfer agent in a range of from about 0.01% to about 0.5% by weight. Examples of anti-dye transfer agents include poly (2-vinylpyridine-N-oxide), poly-2-(dimethylamino)-ethylmethacrylate-N-oxide, and poly-1-vinylimidazole-N-oxide. Other examples of anti-dye transfer agents include carboxyl containing polymers, N-vinyloxazolidone polymers, and copolymers of polyvinylpyrrolidone and acrylic acid nitrile or maleic anhydride. Such dye transfer inhibiting agents are disclosed in U.S. Pat. No. 5,633,225 issued on May 27, 1997.

Optionally, the stress reducing composition may include a corrosion protection additive for the steam iron in a range of from about 0.1% to about 3% by weight. Examples of corrosion protection additives include polyethylene glycol. Other useful corrosion protection additives include cyclohexylamine, diammonium phosphate, dilithium oxalate, dimethyl amino methylpropanol, dipotassium oxalate, dipotassium phosphate, disodium phosphate, disodium pyrophosphate, disodium tetrapropenyl succinate, nitromethane, potassium silicate, sodium aluminate, sodium hexametaphosphate, sodium metasilicate, sodium nitrite, sodium oxalate, sodium silicate, and stearamidopropyl dimethicone. The important point to note is that these corrosion inhibitors are used in dilution with water so that they do not stain the fabric being ironed, desirably in a range of from about 0.1% to about 1% by weight. One skilled in the art can determine the specific amount in dilution with water without undue experimentation.

In the preferred embodiment of the present invention, the composition is adapted to not cause staining of fabrics. This is a critical property of the composition because no matters how good the composition is, from the standpoint of having stress reduction properties, if it stains the fabric being ironed, it will lose its utility value.

In the preferred embodiment of the present invention, the method includes delivering the stress reducing composition into a liquid container of a steam iron and heating the steam iron. This is accomplished by simply plugging the steam iron to an electric outlet and allowing the iron to heat to a normal operating temperature suitable for the fabric to be ironed. At the users option, the stress reducing composition may be further diluted with water, so long as the amount of the volatile natural essential oil present in the water-diluted composition is present in an amount in a range of from about 0.05% to about 5% by weight of the total liquid filled into the liquid container of the steam iron.

In the preferred embodiment of the present invention, the method includes releasing vapors of the stress reducing composition produced within the liquid container of the steam iron upon heating, into ambient air and causing reduction of physiological and/or subjective reactivity to stress in the human by one or more of transdermal ingestion or inhalation of the vapors by the human.

The following Example A is a representative composition of (a) a stress reducing composition, and (b) an aromatherapeutically active composition, suitable for using in the present invention:

EXAMPLE A

| Ingredient | Weight % |
|---|---|
| Volatile essential oil | 2.00 |
| Water | 98.00 |
| Total | 100.00 |

The volatile essential oil has the following composition:

| | |
|---|---|
| Nutmeg Oil East Indian | 97.10 |
| Mace extract | 0.14 |
| Neroli Oil | 0.98 |
| diethyl phthalate | 0.44 |
| Valerian Oil Indian | 0.05 |
| Total | 100.00 |

Accordingly, having thus described the invention in detail, it will be obvious to those skilled in the art that various changes may be made without departing from the scope of the invention and the invention is not to be considered limited to what is described in the specification.

What is claimed is:

1. A method of using steam ironing of a fabric to reduce a human's elevated blood pressure due to stress, the method comprising the steps of:
    a. providing a steam iron containing a stress reducing composition comprising a volatile natural essential oil;
    b. operating the steam iron such that the fabric is ironed and vapors from said stress reducing composition are released into the ambient air surrounding the human such that the human's elevated blood pressure due to stress is reduced upon transdermal ingestion and/or inhalation of said vapors by said human.

2. The method according to claim 1 wherein said stress reducing composition comprises from about 0.05% to about 5% by weight of the composition of the volatile natural essential oil.

3. The method according to claim 2 wherein said stress reducing composition comprises from about 0.5% to about 2% by weight of the composition of the volatile natural essential oil.

4. The method according to claim 1 wherein said volatile natural essential oil is selected from the group consisting of: nutmeg oil, mace extract, neroli oil, valerian oil, myristicin, isoelemicin, elemicin, hops extract, elder flower extract, eucalyptus oil, spearmint oil, clary sage oil, rosewood oil, juniper oil, witch hazel, mentha piperita oil, orange oil, sweet violet leaf oil, cedar-wood oil and mixtures thereof.

5. The method according to claim 4 wherein said volatile natural essential oil is selected from the group consisting of: nutmeg oil, mace extract, neroli oil, valerian oil, myristicin, isoelemicin, elemicin and mixtures thereof.

6. The method according to claim 4 wherein said volatile natural essential oil is selected from the group consisting of: hops extract, elder flower extract, eucalyptus oil, spearmint oil, clary sage oil and mixtures thereof.

7. The method according to claim 4 wherein said volatile natural essential oil is selected from the group consisting of: rosewood oil, juniper oil and mixtures thereof.

8. The method according to claim 4 wherein said volatile natural essential oil is selected from the group consisting of: witch hazel, mentha piperita oil, orange oil, sweet violet leaf oil, hops extract, elder flower extract and mixtures thereof.

* * * * *